United States Patent [19]

Anger et al.

[11] Patent Number: 5,637,565

[45] Date of Patent: Jun. 10, 1997

[54] PURIFIED FORM OF STREPTOGRAMINS, ITS PREPARATION AND PHARMACEUTICAL COMPOSITIONS CONTAINING IT

[75] Inventors: Pascal Anger, Verrières-le-Buisson; Bertrand Bonnavaud, Viroflay; Alain Callet, Orly; Patrick Lefevre, Vincennes, all of France

[73] Assignee: Rhone-Poulenc Rorer S.A., Antony, France

[21] Appl. No.: 472,768

[22] Filed: Jun. 7, 1995

Related U.S. Application Data

[62] Division of Ser. No. 197,984, Feb. 17, 1994, abandoned.

[30] Foreign Application Priority Data

Feb. 17, 1993 [FR] France .................... 93 01787

[51] Int. Cl.⁶ .................... A61K 38/04; A61K 38/08; C07K 1/30; C07K 1/32
[52] U.S. Cl. .................... 514/11; 530/344
[58] Field of Search .................... 530/344; 514/11

[56] References Cited

U.S. PATENT DOCUMENTS

| | | | |
|---|---|---|---|
| 4,618,599 | 10/1986 | Corbet et al. | 514/11 |
| 4,668,669 | 5/1987 | Barriere et al. | 514/183 |
| 4,798,827 | 1/1989 | Barriere et al. | 514/183 |

FOREIGN PATENT DOCUMENTS

| | | |
|---|---|---|
| 0 506 561 | 9/1992 | European Pat. Off. . |
| 2 619 008 | 2/1989 | France . |

OTHER PUBLICATIONS

J. Preud'Homme, et al., "Pristinamycine isolement, caracterisation et identification des constituants", pp. 585–591, Bulletin de la Societe Chimique de France, 1968, vol. 2.

N.K. Sharma et al., "Isolation of factor A (viginamycin M1) and factor B (mixture of VS1 and VS4) from a commercial fee additive formulation", Chemical Abstracts, vol. 110, No. 7, Feb. 13, 1989, abstract No. 56082.

*Primary Examiner*—Jerry D. Johnson
*Attorney, Agent, or Firm*—Finnegan, Henderson, Farabow, Garrett & Dunner, L.L.P.

[57] ABSTRACT

This invention relates to a purified form of streptogramins, consisting of a combination of one or more group B components of streptogramins, of general formula:

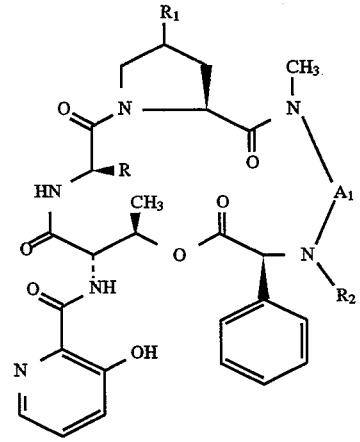

in which $A_1$ is a radical of general formula:

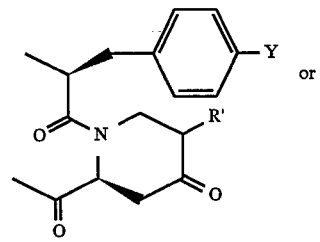

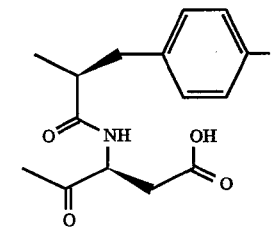

for which R' is H or OH and Y is H, a methylamino radical or a dimethylamino radical, R is an ethyl radical or, when R' is H, R can also represent —$CH_3$, and $R_1$ and $R_2$ are H, or alternatively $A_1$ is a radical of formula:

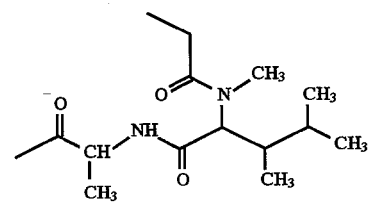

R is an isobutyl radical, and $R_1$ is OH and $R_2$ is —$CH_3$, and one or more group A minority components of streptogramins, of general formula:
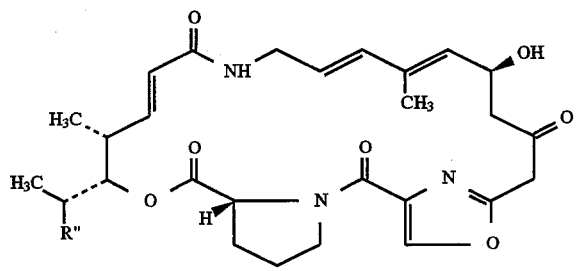
in which R" is H or a methyl or ethyl radical, in the state of cocrystallizate, of a coprecipitate or of a physical mixture of the powders.
24 Claims, No Drawings

PURIFIED FORM OF STREPTOGRAMINS, ITS PREPARATION AND PHARMACEUTICAL COMPOSITIONS CONTAINING IT

This is a divisional of application Ser. No. 08/197,984 filed Feb. 17, 1994 now abandoned.

FIELD OF THE INVENTION

The present invention relates to a purified form of streptogramins comprising at least one group B component of streptogramins combined with at least one group A "minority" component defined below by the general formula (II).

BACKGROUND OF THE INVENTION

Among known streptogramins, pristinamycin (RP 7293), an antibacterial of natural origin produced by *Streptomyces pristinaespiralis*, was isolated for the first time in 1955. Pristinamycin marketed under the name Pyostacine® consists mainly of pristinamycin IA and pristinamycin IIA.

Another antibacterial of the streptogramin class, namely virginiamycin, has been prepared from *Streptomyces virginiae*, ATCC 13161 [Antibiotics and Chemotherapy, 5, 632 (1955)]. Virginiamycin (Staphylomycine®) consists mainly of factor S and factor $M_1$.

In U.S. Pat. No. 3,325,359, pharmaceutical compositions comprising antibiotic substances constituting antibiotic 899, namely factor S and factor $M_1$, have been described.

In Patent Application FR 2,619,008, the use of group A and group B components for the treatment of ache has been described.

The antibacterials of natural origin of the streptogramin class consist of a mixture of 2 groups of components: group B components and group A components, each group having an antibacterial activity of its own. It has been demonstrated that the combination made up of the 2 groups of components produces a synergy of action which results in an enhanced bacteriostatic and bactericidal activity and in a broadening of the spectrum of activity.

In Streptogramine als Modelsysteme für den Kationentransport durch Membranen, Dissertation zur Erlangung des Doktorgrades der Mathematisch-Naturwissenschaftlichen Facultät der Georg-August Universität zu Göttingen, Göttingen 1979, in Antibiotics III, 521 (1975) and in Antibiotics of the virginiamycin family, Inhibitors which contain synergistic components, C. Cocito, Microbiological Reviews, 145–98 (1979), groups A and B components of streptogramins have been described. J. Preud'Homme, P. Tarridec and A. Belloc, Bull. Soc. Chim. Fr., 2, 585 (1968) have also described natural pristinamycin as well as the different components of which it is made up.

All attempts to make purified combinations of streptogramins invariably involve the group A majority component [pristinamycin IIA (PIIA)] which is considered to be responsible for the activity and for the synergy of action. The conclusion from some studies has pointed, moreover, to the importance of this component, which produces better synergy: EP 506,561 (page 2).

However, these attempts have never been crowned with success, on the one hand because of the difficulties of industrial preparation, and most of all because purified pristinamycin IIA is a crystallide product whose bioavailability has proved to be too low for it to be possible to envisage making it the active principle of a medicinal product.

From the standpoint of the industrial preparation of such products, the techniques available had not hitherto made it possible to obtain, on a preparative scale, a sufficiently purified form and the production of batches of sufficiently constant and reproducible quality to satisfy the requirements of the laws of some countries concerning registration.

As an example, industrial batches of natural pristinamycin contain, after purification, an amount of impurities which can reach 20%. The attempts at purification carried out hitherto have invariably ended in failure and very often in degradation of one of the groups of components, because these are labile products for which many operations lead to opening of the ring structure or to dehydration of the group A components. As a result, for many years it was considered that an improvement in the degree of purity could not be achieved. In 1988, purification was still considered to be a problem: J. of Liq. Chromatography, 11 (11), 2367 (1988). Also in 1988, N. K. SHARMA and M. J. O. ANTEUNIS likewise declared that separation and purification of the components of virginiamycin were possible for analytical purposes, but could not be envisaged for the production of the products in view of the difficulties encountered: Bull. Soc. Chim. Belg., 97 (3) 193 (1988).

In consequence of this situation, the marketing of pristinamycin (Pyostacine®) was irrevocably limited to certain countries such as France and Belgium. The same applied to virginiamycin (Staphylomycine®), marketed only in a limited number of countries in relation to human medicine, as well as to mikamycin whose marketing (limited to Japan) has now been stopped. This has hence resulted in some populations being deprived of the treatment in the case of severe infections caused by Gram-positive cocci (in particular infections caused by methicillin-resistant staphylococci), or of the treatment in the case of sexually transmitted diseases.

In the field of antibacterials, it is well known by practitioners that allergies or resistances may develop after administration of some classes of antibiotics [The New England Journal of Medicine, 324 (9), 601 (1991)]. In the hospital environment, many resistant strains of *Staphylococcus aureus* are known in particular. For this reason, it is extremely useful for the doctor to have at his disposal a wide range of chemically different classes so as to be able to match the treatment to the particular case of the patient to be treated. The consequence of the failure of a particular class to be marketed can be very serious, or even dramatic, since it can result in patients who do not tolerate the other classes of antibiotic being deprived of treatment.

Thus, the attempts made at purification had always been directed towards removing the minority components of streptogramins, these being regarded as non-essential and, for the most part, as impurities.

Among the group A components of natural streptogramins, pristinamycin IIB (PIIB) is a minority component whose proportion by weight is less than 10% in natural pristinamycin, and most often of the order of 8% or even of the order of 6% in virginiamycin.

DESCRIPTION OF THE INVENTION

It has now been found, and this forms the subject of the present invention, that the combination consisting of one or more group B components of general formula:

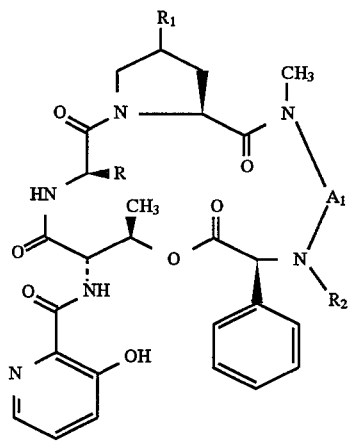

in which A₁ is a radical of general formula:

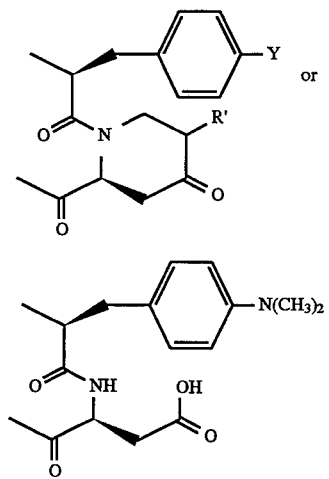

for which

R' is a hydrogen atom or a hydroxyl radical and Y is a hydrogen atom, a methylamino radical or a dimethylamino radical, R is an ethyl radical or, when R' represents a hydrogen atom, R can also represent a methyl radical, and R₁ and R₂ represent a hydrogen atom, or alternatively A₁ is a radical of formula:

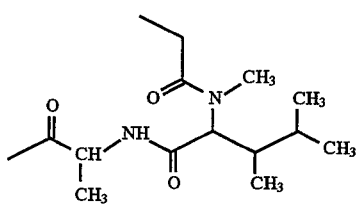

R is an isobutyl radical, and

R₁ is a hydroxyl radical and R₂ is a methyl radical, and one more group A "minority" components of general formula:

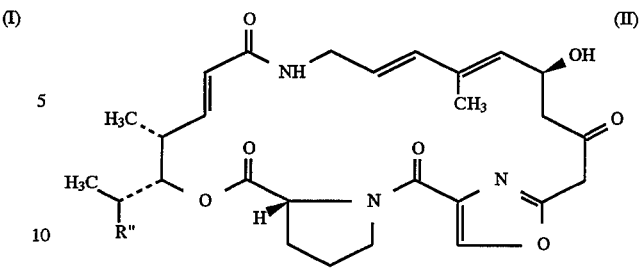

in which

R" is a hydrogen atom or a methyl or ethyl radical, is especially advantageous on account of its biological activity in vivo.

In effect, the combinations according to the invention manifest a biological action in vivo which is markedly greater than that of the natural product (for example natural virginiamycin or natural pristinamycin) or than that of combinations involving the group A majority component, and are, most particularly, endowed with altogether satisfactory bioavailability. Furthermore, these combinations may be prepared on a large scale.

It is thus possible to gain access to a purified and bioavailable form of a final product having a good level of activity and containing less than 6% of impurities.

The product of general formula (II) for which R" is an ethyl radical, hereinafter referred to as pristinamycin IIF (PIIF), and the product of general formula (II) for which R" is a hydrogen atom, hereinafter referred to as pristinamycin IIG (PIIG), are new products which constitute streptogramin components of very low abundance, the proportion of which by weight is less than 0.5% in the batches of natural product.

The combinations according to the invention are advantageously prepared in proportions of 10:90 to 90:10 (by weight), or preferably in the proportions of 20:80 to 80:20. They occur in the state of a physical mixture of the powders, but also, and this constitutes a further aspect of the present invention, in the state of a coprecipitate; or alternatively, according to a third aspect of the invention, in the state of a cocrystallizate as defined below.

The present invention also relates to the purified forms consisting of the cocrystallized combination of at least one group B component of general formula (I) with at least one group A component defined by the general formula (II).

The cocrystallisation takes place in the constant stoichiometry of 1 mol of component(s) of general formula (I) with 2 mol of group A component(s) of general formula (II) [this stoichiometry corresponding to the relative proportion of approximately 43–44:57–56 by weight in the case where the component A is a product of general formula (I) for which A₁ is of structure (Ia)].

The cocrystallized combination according to the invention may alternatively be used as a purified and stable antimicrobial agent also possessing improved in vivo activity as well as good bioavailability, or else as a means of purification of a minority component of streptogramins corresponding to the general formula (II).

In effect, it has never been possible to purify a group A component of general formula (II) by crystallization; as a result, hitherto, only chromatographic methods were known for preparing a purified group A product of general formula (II), and no other means of purification was known to enable these products to be isolated in large Amounts.

It has now been shown that the group A component of general formula (II) may be obtained in the pure state by proceeding via the cocrystallized combination defined above. A crude mixture containing at least 30% of a group A minority component corresponding to the general formula (II), dissolved in an organic solvent such as a ketone (acetone, methyl ethyl ketone, methyl isobutyl ketone, for example), an ester (ethyl acetate, isopropyl acetate, butyl acetate, isobutyl acetate, for example), a chlorinated solvent (methylene chloride, chloroform, 1,2-dichloroethane, for example), or a nitrile (acetonitrile for example), and to which a group B component defined by the general formula (I) is added, gives a cocrystallized compound in the proportions defined above. It is understood that the amount of compound of general formula (I) introduced is appropriately chosen so that the residual concentration of this product (after the cocrystallization) is less than its solubility in the medium. It is also understood that variations in the respective contents of the initial medium with respect to the product of general formula (II) and with respect to the product of general formula (I) do not bring about a modification of the cocrystallized compound obtained. The cocrystallized combination thereby obtained, dissolved in a solvent such as, for example, methyl isobutyl ketone or dichloroethane and treated in an acid medium (sulphuric acid, hydrochloric acid, for example), makes it possible to obtain, after treatment of the organic phase with a solvent such as, for example, hexane, the group A minority component purified and free from group B component.

This cocrystallized combination affords, moreover, the advantage of a greatly enhanced stability and a high purity and, most particularly, of readily permitting industrialization.

It should be clear that this method may also be adapted to the preparation of cocrystallizates with modified derivatives of the natural group B components of streptogramins, and that these cocrystallizates also fall within the scope of the present invention; similarly, the preparation of the purified forms of minority components of general formula (II) from such cocrystallizates also falls within the scope of the present invention.

A preferred embodiment of the invention relates to a combination of pristinamycin IB [as defined above when $A_1$ represents a radical of general formula (Ia) for which Y is a methylamino radical and R' is a hydrogen atom, and R is an ethyl radical] or of virginiamycin $S_1$ [as defined above when $A_1$ represents a radical of general formula (Ia) for which Y and R' are hydrogen atoms, and R is an ethyl radical] or of a mixture of virginiamycin $S_1$ and virginiamycin $S_4$ [as defined above when $A_1$, is defined as for virginiamycin $S_1$ and R is a methyl radical] with pristinamycin IIB [as defined above by the general formula (II) in which R" is methyl] and containing less than 6% of impurities, and preferably less than 3% of impurities.

A preferred embodiment of the invention also relates to a purified streptogramin consisting of the combination of a group B component of streptogramins defined by the general formula (I) and a group A component of general formula (II) containing a relative proportion of the groups B and A components in a constant mole ratio of the order of 1:2.

According to the invention, the new combinations of at least one group B component of streptogramins of general formula (I) and at least one group A component of general formula (II) may be obtained, for example, by preparation of the cocrystallized compound as is defined above. When it is desired to obtain a combination in different proportions, the cocrystallized compound thus prepared may be combined with at least one of the components of general formula (I) or with at least one group A component of general formula (II), these components being purified beforehand and in an appropriate amount for obtaining the desired proportions, or else the group A component of general formula (II) (or mixture of such components) may be purified from the cocrystallizate and then mixed in the desired proportions with one or more group B components of general formula (I). Alternatively, the combinations according to the invention may be prepared after isolation of the group B component(s) and of the group A component of general formula (II) from the corresponding natural streptogramin, by purification of each of these components, followed by mixing of the purified components in the desired proportions as are defined above.

The combinations according to the invention may also be coprecipitated in the desired proportions from a solution of the components of general formulae (I) and (II) [or alternatively from a solution of the cocrystallizate and of one of the components of general formula (I) or (II)] in methyl isobutyl ketone or in acetone or methylene chloride, the solution being poured into hexane or cyclohexane or into water.

The preparation and separation of the groups A and B components are performed by fermentation and isolation of the constituents from the fermentation must according to or by analogy with the method described by J. Preud'homme et al., Bull. Soc. Chim. Fr., vol. 2, 585 (1968), in Antibiot. & Chemother., 5, 632 (1955) or 7, 606 (1957), in Chromatog. Sym., 2° Brussels, 181 (1962), in Antibiot. Ann., 728 784 (1954–55), in U.S. Pat. No. 3,299,047 or in Streptogramine als Modelsysteme für den Kationentransport durch Membranen, Dissertation zur Erlangung des Doktorgrades der Mathematisch-Naturwissenschaftlichen Facultät der Georg-August Universität zu Göttingen, Göttingen 1979, or as described below in the examples. In particular, in the case of pristinamycins, the separation of the groups A and B components is performed by suspending crude streptogramin in an organic solvent such as an acetate (ethyl acetate for example), followed by filtration or centrifugation of the crude group A component and by extraction of the group B component in an acidic aqueous medium followed by a re-extraction in a methylene chloride medium. The separation of groups A and B components may also be performed by acid extraction of a solution of crude streptogramin in methyl isobutyl ketone, followed by isolation by extraction of the group B component from the aqueous phase and isolation of the group A component by precipitation from the organic phase.

After separation, purification of the group B components of streptogramins may be carried out by crystallization in an alcohol such as ethanol, methanol or isopropanol, in an acetate (isopropyl acetate or butyl acetate, for example), in a ketone (methyl ethyl ketone for example) or in acetonitrile, or by chromatography. Purification of the group A components of general formula (II) may be performed by chromatography, eluting with an acetonitrile/water mixture.

Alternatively, the preparation of the groups A and B components of general formulae (II) and (I), respectively, is performed as described in French Patent Application 2,689, 518, by separate fermentation according to the following steps:

first step (optional), mutagenesis on a non-selective microorganism producing streptogramins, and second step, selection of the selective microorganisms.

The non-selective microorganisms are generally actinomycetes and fungi. The starting microorganisms which can be used in the process are, in particular, microorganisms which are non-selective producers of a streptogramin chosen from the group comprising pristinamycin, virginiamycin, mikamycin, ostreogrycin, viridogrisein, vernamycin and etamycin. As an example, some non-selective microorganisms which may be employed are named below in the table.

| MICROORGANISMS | ANTIBIOTICS |
|---|---|
| FUNGI | |
| *Micromonospora Sp.* | vernamycin |
| STREPTOMYCES | |
| *S. alborectus* | virginiamycin |
| *S. griseus* (NRRL2426) | viridogrisein |
| *S. lavendulae* | etamycin |
| *S. loidensis* (ATCC11415) | vernamycin |
| *S. mitakaensis* (ATCC15297) | mikamycin |
| *S. ostreogriseus* (ATCC27455) | ostreogrycin |
| *S. pristinaespiralis* (ATCC25486) | pristinamycin |
| *S. virginiae* (ATCC13161) | virginiamycin |
| ACTINOMYCES | |
| *A. daghestanicus* | etamycin |

More especially, the preparation is carried out from microorganisms chosen from *Streptomyces alborectus, Streptomyces mitakaensis, Streptomyces pristinaespiralis, Streptomyces ostreogriseus* and *Streptomyces virginiae*.

The first step of the preparation consists in modifying the non-selective microorganism so as to increase its overall capacity for antibiotic production and/or so that it synthesizes only one of the two components of streptogramins. This may be obtained by genetic modifications (mutation in structural genes for enzymes involved in the pathway of biosynthesis, or in sequences permitting the expression of such structural genes, for example) or biochemical modifications (modification of a post-translational mechanism, impairment of a feedback-inhibition mechanism, and the like). Various mutagenesis tools are used:

physical agents: X-rays, ultraviolet rays; or chemical agents: alkylating agents such as ethyl methanesulphonate (EMS), N-methyl-N'-nitro-N-nitrosoguanidine (Delic et al. Mutation Res. 9 (1970) 167–182) or 4-nitroquinoline 1-oxide (NQO); bialkylating agents; intercalating agents; or any system of mutational insertion into DNA, and especially transposons, integrative plasmids, phages or prophages; or alternatively protoplast fusion (Cohen, Nature 268 (1977) 171–174).

These tools (alone or in combination) may be applied to the non-selective microorganisms in the state of spores or of germinated or germinating spores, or to mycelium. The preparation may also make use of manipulations (at random or directly) that enable microorganisms capable of selectively producing one component of streptogramins from non-selective micro-organisms to be obtained.

The second step of the preparation relates to the identification and isolation of the selective microorganisms. This step may be carried out, in particular, by means of a test of sensitivity with respect to a microbe. Various microbes which are specifically sensitive to group A components or to those of group B of streptogramins exist: for example, *Bacillus subtilis* (ATCC6633), *Bacillus circulans, Bacillus cereus* (Watanabe, J. Antibio. Ser. A XIII(1) (1960) 62) or *C. xerosis* (Watanabe, loc. cit.), which are specifically sensitive to group B components; *Streptococcus agalactiae* B96 (Antimicrob. Agents Chemother. 10(5) (1976) 795), *Micrococcus luteus* (Prikrylova, loc. cit.) or *Sarcina lutea* (ATCC9341), which are specifically sensitive to group A components. It is also possible to prepare artificially microbes which are specifically sensitive to one component of streptogramins by inserting a gene for resistance to one of the 2 components of streptogramins into a microbe which is sensitive to both of them. Some of these genes have been cloned (Le Goffic et al., J. Antibio. XXX(8), 665 (19771; Le Goffic et al., Ann. Microbiol. Inst. Pasteur 128B, 471 (1977); Solh et al., Path. Biol. 32(5), 362, (1984)); such genes are introduced into different microbes by standard techniques of molecular biology. The selection step my also be performed by an ELISA test using specific antibodies for the components A or B, or alternatively by analytical techniques such as chromatography (liquid chromatography, thin-layer chromatography, and the like). In the case of a test of sensitivity with respect to a microbe, it is, in addition, preferable to validate the selection by chromatographic assay.

Thus, according to the invention, it is now possible to obtain on an industrial scale a new purified form of streptogramin in which the level of impurities, the definition and the constancy of the composition complies with the requirements of the registration laws, and which furthermore possesses improved in vivo activity and bioavailability as well as lower toxicity. The new combination may thus remedy the lack of treatment with an antibacterial of this class in many countries.

The new combination of a group B component of streptogramins of general formula (I) and a group A component of streptogramins of general formula (II) displays especially advantageous in vivo activity against Gram-positive microbes in particular. In vivo, in mice, it was shown to be active against *Staphylococcus aureus* IP 8203 at doses of 30 to 50 mg/kg administered orally.

As an example, the oral $CD_{50}$ of several combinations of the components of general formulae (I) and (II) in the experimental *Staphylococcus aureus* IP 8203 infection of mice is given below.

In Table I below, the combinations studied are prepared by coprecipitation in hexane from a solution of the components of general formulae (I) and (II) in methyl isobutyl ketone or in acetone:

TABLE I

| Product (I)/product (II) combination: PI (Example 1)/PIIB (Example 18) | $CD_{50}$ (mg/kg) p.o. |
|---|---|
| 10:90 | 44 |
| 20:80 | 32 |
| 30:70 | 30 |
| 70:30 | 30 |
| 80:20 | 30 |
| 90:10 | 50 |

In Table II below, the combinations illustrated are cocrystallized products prepared as described in the examples.

TABLE II

| Cocrystallized product (I)/ product (II) combination | $CD_{50}$ (mg/kg) p.o. |
|---|---|
| PI/PIIB (Example 9) | 38 |
| PIA/PIIB (Example 11) | 28 |
| PIB/PIIB (Example 12) | 32 |
| PIC/PIIB (Example 13) | 36 |
| PID/PIIB (Example 14) | 50 |
| Factor S/PIIB (Example 15) | 32 |
| Factor $S_1$/PIIB (Example 16) | 50 |
| Factor S/PIIF (Example 17) | 50 |

In Table III below, the combination described is prepared in the form of a physical mixture of the powders.

TABLE III

| Product (I)/product (II) combination | CD$_{50}$ (mg/kg) p.o. |
|---|---|
| PIA (Example 1)/PIIB (Example 18) 30:70 | 36 |
| PIA (Example 1)/PIIB (Example 18) 50:50 | 40 |
| Factor S (Example 5)/PIIB (Example 18) 30:70 | 44 |

Furthermore, the new combination does not display toxicity: no sign of toxicity manifests itself in mice at a dose of 150 mg/kg administered orally (2 administrations).

According to the invention, when the cocrystallized combination is used as a means of purification of the component of general formula (II), the latter may be obtained by acid extraction of a solution of the cocrystallized compound in a ketone (methyl isobutyl ketone for example), followed by isolation by extraction of the group A component by precipitation from the organic phase.

EXAMPLES

The examples which follow, given without implied limitation, illustrate the present invention.

In the examples which follow, it is understood that the assays are given in % by weight.

SEPARATION AND PURIFICATION OF GROUP B COMPONENTS:

Example 1

30 kg of crude pristinamycin [pristinamycin IA (PIA): 20.7%, pristinamycin IB (PIB): 3.9%, pristinamycin IC (PIC): 0.6%, pristinamycin ID (PID): 0.3%, pristinamycin IIB (PIIB): 8%, pristinamycin IIA (PIIA): 45%, pristinamycin IIF (PIIF): <0.5% (not assayed), pristinamycin IIG (PIIG): 0.5% (not assayed)] are suspended in 210 liters of ethyl acetate and stirred for 15 hours at room temperature. The suspension is filtered and the ethyl acetate filtrate is collected and extracted with twice 20 liters of 1N sulphuric acid and then 20 liters of distilled water. The combined aqueous phases are washed with 6 times 15 liters of ethyl acetate, then adjusted to pH 7 by adding 30 liters of 10% sodium bicarbonate solution and extracted with 3 times 30 liters of methylene chloride. The methylene chloride phases are combined and washed with 10 liters of distilled water. The methylene chloride is then distilled off and replaced by 50 liters of ethanol. The mixture is then treated under reflux with 0.8 kg of L3S charcoal for 30 minutes. After filtration and washing with twice 5 liters of ethanol, the mixture is cooled to 10° C. in the course of 15 hours. After being maintained for one hour at 10° C. the suspension is filtered and washed with 3 times 7 liters of ethanol. After drying of the solid at 40° C. under reduced pressure, 5.7 kg of purified pristinamycin I (hereinafter referred to as PI) are obtained.

Assay: 96.8% (PIA: 81.1%, FIB: 12%, PIC: 2.6%, FID: 1.1%);

Yield with respect to PIA: 74%.

1500 g of purified PI are taken up with 9 liters of 1,2-dichloroethane, and 1.5 equivalents of succinic anhydride and 0.015 equivalent of dimethylaminopyridine are then added. The solution is maintained for 1 week at 20° C. and then introduced onto a column containing 10 kg of silica (20–45 µm) [column height: 1 m; diameter: 20 cm]. Elution is performed by percolation of a 1,2-dichloroethane/methanol mixture at a flow rate of 18 liters/hour for 6 hours; the percentage of methanol (water content 5%) is increased from 0 to 4% during the chromatographic run. 47 2.4-liter fractions are recovered.

Fractions 5 to 15 are pooled, and the 1,2-dichloroethane is evaporated off and replaced by 5 liters of ethanol. After crystallization, 365 g of PIA assaying at 99.8% are obtained.

Example 2

Fractions 36 to 39 from the chromatographic run described in Example 1 are pooled and the 1,2-dichloroethane is distilled off; 210 g of solid are thereby obtained. 40 g of this solid are taken up with 8 liters of water to which 8 cm$^3$ of 10N hydrochloric acid are added. After 3 hours at 90° C., the solution is neutralized to pH 6.5 with sodium hydrogen carbonate. The solution is extracted with 3 times 1 liter of ethyl acetate and the extract is washed with twice 0.2 liter of water. After treatment with charcoal, the ethyl acetate is evaporated off and replaced by 600 cm$^3$ of ethanol. After recrystallization, 20 g of PIB assaying at 97% are obtained.

Example 3

Fractions 22 to 26 from the chromatographic run described in Example 1 are pooled and the 1,2-dichloroethane is distilled off; 139 g of solid are thereby obtained. This solid is taken up with a minimum of 1,2-dichloroethane and introduced onto a silica column. Elution is performed by percolation of a 1,2-dichloroethane/methanol mixture at a flow rate of 18 liters/hour for 6 hours; the percentage of methanol (water content 5%) is increased from 0 to 5% during the chromatographic run. 48 2.4-liter fractions are recovered. Fractions 38 to 43 are evaporated and the solid is taken up with 300 cm$^3$ of ethanol. After recrystallization, 22 g of PI containing 40% of PIC are obtained. Successive chromatographic runs on silica (20–45 µm) with percolation using a methylene chloride/methanol (98:2 by volume) eluent enable 5 g of a solid to be obtained, which solid, after vigorous agitation with methyl isobutyl ketone and recrystallization in ethanol, assays at 95% with respect to PIC.

Example 4

1000 g of PI, obtained as described above in Example 1, are dissolved in the minimum of chloroform and purified in successive fractions on a column of silica (20–45 µm). After elution with chloroform containing 2 to 5% of methanol, a product is obtained and is concentrated to dryness. This product is then purified by 2 successive runs on a column of Diaion® resin percolated with an acetonitrile/water (60:40 by volume) mixture. The fractions are monitored by chromatography. The fractions containing PID are pooled and concentrated to dryness. Approximately 3 g of product assaying at 60% with respect to PID are thereby obtained. A further purification is performed by countercurrent chromatography using a methyl isobutyl ketone/acetone/formic acid (40:2:40 by volume) solvent mixture. Concentration of the fractions containing PID to dryness enables 1 g of solid assaying at 95% with respect to PID to be obtained.

Example 5

400 g of Staphylomycine® (in tablet form—initial composition: virginiamycin S$_1$ (S$_1$): 3.4%, virginiamycin S$_4$ (S$_4$): 0.9%) are introduced into 4 liters of water.

The tablets are disintegrated by stirring for 15 minutes at 20° C. 1 liter of methylene chloride is added and stirring is continued for 1 hour. Next, after settling has taken place, the methylene chloride phase is separated and filtered and is then run in the course of 30 minutes into a volume of 5 liters of stirred hexane. After 1 hour of stirring, the suspension is filtered and a solid is collected and washed with 3 times 250 cm$^3$ of hexane. After drying, 52 g of solid are recovered and suspended in 370 cm$^3$ of ethyl acetate. The suspension is agitated vigorously twice in succession at 20° C. and for a period of 18 hours. The filtrate corresponding to each agitation treatment is taken to dryness and then dissolved in 850 cm$^3$ of methanol under reflux. After a gradual fall in the temperature to −20° C. in the course of 16 hours, a solid is collected by filtration and washed with a small amount of methanol. After drying of the solid at 35° C. under reduced pressure, 9 g of factor S (virginiamycin S) are obtained.

Assay: 96% ($S_1$: 75.4%, $S_4$: 20.6%).

Yield with respect to factor $S_1$ (virginiamycin $S_1$): 50%.

Example 6

1 g of factor S, obtained as described above in Example 5 and dissolved in acetonitrile in the proportion of 125 mg/cm$^3$, is purified in 4 operations by chromatography on a Nucleosil 5C8® column (height 25 cm, external diameter 2.54 cm), injecting a volume of 2 cm$^3$ and eluting with a water/acetonitrile (60:40 by volume) mixture at a flow rate of 7.5 cm$^3$/minute. On each occasion, a volume of 120 cm$^3$ containing factor $S_1$ is collected, equivalent to 480 cm$^3$ in all. The chromatographic procedure is repeated 4 times in order to treat the whole of the 1 g of factor S. A volume of approximately 500 cm$^3$ containing factor $S_1$ is thereby collected. The acetonitrile is removed using a rotary evaporator. The aqueous phase is extracted with 3 times 50 cm$^3$ of dichloromethane. The methylene chloride phases are combined, washed with 50 cm$^3$ of distilled water, dried over sodium sulphate and filtered. The dichloromethane is eliminated using a rotary evaporator under reduced pressure (5 mm of mercury). 0.67 g of factor $S_1$ assaying at 99.6% is thereby obtained.

PREPARATION OF CRUDE GROUP A COMPONENTS:

Example 7

500 g of crude pristinamycin [pristinamycin IA (PIA): 20.7%, pristinamycin IB (PIB): 3.9%, pristinamycin IC (PIC): 0.6%, pristinamycin ID (PID): 0.3%, pristinamycin IIB (PIIB): 8%, pristinamycin IIA (PIIA): 45%) are dissolved in 50 liters of methyl isobutyl ketone. This solution is extracted 5 times with an aqueous phase composed of 2.5 liters of water and 2.5 liters of 1N sulphuric acid, and then washed with 3 times 10 liters of water. The methyl isobutyl ketone is then treated with 7.5 liters of an aqueous sodium hydrogen carbonate solution containing 35 g/liter, and then washed with 5 liters of water. On each occasion, the aqueous phase is mixed with the organic phase, settling is allowed to take place and the aqueous phase is separated.

The organic phase obtained is brought into contact with 750 g of alumina, filtered, concentrated to a volume of approximately 4 liters and taken up with 5 volumes of hexane. The precipitate obtained is filtered off and dried. 300 g of product are obtained, which product is suspended in 1 liter of isopropanol. After stirring at 55° C. for 45 minutes, the suspension is filtered at 4° C. The filtration mother liquors are concentrated to dryness, and the residue is taken up with 500 cm$^3$ of methyl isobutyl ketone into which 5 volumes of hexane are poured. The precipitate is filtered off, washed with hexane and dried at 40° C. under reduced pressure. 69 g of crude PIIB, containing 36% of PIIB and 6% of PIIA and no longer containing PIA, are obtained.

Example 8

60 g of crude PIIB, obtained as above in Example 7, are purified in several operations by chromatography on a Nucleosil 5C8® column (column diameter 5 cm, height 30 cm) percolated with a 60:48 water/acetonitrile eluent. 250 mg of pristinamycin IIF (PIIF) are thereby obtained.

PREPARATION OF A COCRYSTALLIZED PRODUCT:

In the examples which follow, it has been demonstrated that the X-ray diffraction spectrum of the cocrystallized product is different from the spectrum of the group B component crystallized alone in the same solvent, where this component exists.

Example 9

Crude PIIB, obtained above in Example 7, is dissolved in 190 cm$^3$ of acetone. 33 g of purified PI (PIA: 81.1%, PIB: 12%, PIC: 2.6%, PID: 1.1%) are added. After 17 hours of stirring at 20° C., a suspension is obtained which is filtered at 4° C. The product is washed and dried. After recrystallization at a concentration of 100 g/l in acetone, 10 g of white crystals are obtained assaying at 55% with respect to PIIB+PIIF+PIIG and assaying at 43% with respect to PIA+PIB+PIC+PID.

Example 10

250 mg of purified PIIB, obtained as described below in Example 18, are dissolved in 17 cm$^3$ of ethyl acetate. 300 mg of purified PI (PIA: 81.1%, PIB: 12%, PIC: 2.6%, PID: 1.1%) are added. After 20 hours of stirring at 20° C., filtration, washing and drying, 125 mg of white crystals are obtained. Assay with respect to PIIB+PIIF+PIIG: 56%; of which PIIB 54%.

Assay with respect to PIA+PIB+PIC+PID: 43%.

Example 11

560 mg of pure PIIB, obtained as described below in Example 18, are dissolved in 5 cm$^3$ of acetone. 480 mg of PIA (assay 99.8%) are added. After 20 hours of stirring at 20° C., the suspension is filtered. After washing with 1 cm$^3$ of acetone and drying for 30 hours at 40° C. under reduced pressure (<1 kPa), 590 mg of white crystals are obtained. Assay with respect to PIIB+PIIF+PIIG: 56%; of which PIIB 54%.

Assay with respect to PIA: 43%.

The mother liquors from the above crystallization are taken up and a further 560 mg load of PIIB is added. The PIIB/PIA mass ratio is then in the region of 4. After 20 hours of stirring, filtration, washing and drying, 195 mg of crystals, of identical purity and composition to those of the crystals originating from the 1st crop, are obtained.

Example 12

Using the procedure described above in Example 11, but replacing PIA by 480 mg of PIB (assay 97%), 820 mg of white crystals are obtained assaying at 56% with respect to PIIB+PIIF+PIIG (of which PIIB 54%) and assaying at 43% with respect to PIB.

Example 13

Using the procedure described above in Example 11, but employing 680 mg of PIIB and 580 mg of PIC (assay 95%)

in 4 cm³ of acetone, 315 mg of white crystals are obtained assaying at 57% with respect to PIIB+PIIF+PIIG (of which PIIB 55%) and assaying at 42% with respect to PI (of which 37% PIC).

Example 14

Using the procedure described above in Example 11, but replacing PIA by 480 mg of PID (assay 95%), 475 mg of white crystals are obtained assaying at 55% with respect to PIIB+PIIF+PIIG (of which PIIB 53%) and assaying at 39% with respect to PID.

Example 15

Using the procedure described above in Example 11, but employing 450 mg of PIIB and 380 mg of factor S (S₁: 75.4%, S₄: 20.6%) in 4 cm³ of acetone, 550 mg of white crystals are obtained assaying at 58% with respect to PIIB+PIIF+PIIG (of which PIIB 56%) and assaying at 41% with respect to factor S (of which 37% S₁).

Example 16

Using the procedure described above in Example 11, but replacing PIA by 480 mg of factor S₁, 750 mg of white crystals are obtained assaying at 58% with respect to PIIB+PIIF+PIIG (of which PIIB 54%) and assaying at 41% with respect to factor S₁.

Example 17 using the procedure described above in Example 11, but employing 224 mg of PIIF and 192 mg of factor S in 2 cm³ of acetone, 220 mg of white crystals are obtained assaying at 55% with respect to PIIF and assaying at 39% with respect to factor S (of which factor S₁: 31%, factor S₄: 5%).

X-ray diffraction diagrams of the products of Examples 9 to 17:

Table IV below shows the relative intensities of the main lines. The X-ray diffraction diagrams are obtained using a Phillips PW1700 diffractometer with a cobalt anticathode. The 15.8 Å line is assigned the reference value 100. The relative values are estimated by measuring the height of the line after deduction of the continuous background.

TABLE IV

| inter-planar spacing (Å) | Product of Example | | | | | | | |
|---|---|---|---|---|---|---|---|---|
| | Ex. 9 | Ex. 11 | Ex. 12 | Ex. 13 | Ex. 14 | Ex. 15 | Ex. 16 | Ex. 17 |
| 15.8 | 100 | 100 | 100 | 100 | 100 | 100 | 100 | 100 |
| 11.8 | 40 | 34 | 35 | 32 | 43 | 28 | 36 | 21 |
| 10.3 | 69 | 52 | 63 | 65 | 50 | 70 | 80 | 87 |
| 9.7 | 38 | 45 | 47 | 44 | 43 | 40 | 49 | 45 |
| 6.4 | 44 | 41 | 51 | 41 | 37 | 40 | 51 | 39 |
| 6.1 | 38 | 41 | 40 | 38 | 43 | 30 | 40 | 35 |
| 5.9 | 75 | 64 | 70 | 63 | 67 | 74 | 89 | 71 |
| 5.8 | 38 | 39 | 47 | 49 | 50 | 44 | 54 | 35 |
| 5.2 | 92 | 75 | 79 | 71 | 70 | 70 | 91 | 81 |
| 5.0 | 67 | 59 | 60 | 60 | 57 | 54 | 69 | 52 |
| 4.7 | 50 | 43 | 53 | 49 | 47 | 50 | 40 | 42 |

The X-ray diffraction diagrams are similar irrespective of the cocrystallized product (the interplanar spacings of the main lines are not significantly different).

PURIFICATION OF A GROUP A COMPONENT:

Example 18

9.3 g of the product obtained in Example 9 are dissolved in 490 cm³ of methyl isobutyl ketone. This solution is extracted twice with 370 cm³ of 0.5N aqueous sulphuric acid solution and then washed with twice 150 cm³ of water. The organic phase is then concentrated to a volume of approximately 80 cm³ and poured into 5 volumes of hexane. The precipitate obtained is washed, filtered off and dried. To remove the methyl isobutyl ketone, the precipitate is then taken up at a concentration of 100 g/l in acetone, poured into 10 volumes of hexane, washed and dried. 3.5 g of a product containing purified PIIB and no longer containing PI are obtained.

Assay PIIB+PIIF+PIIG: approximately 95%, of which 92% PIIB.

The present invention also relates to pharmaceutical compositions which can be used in human or veterinary medicine and which contain as active product the new purified streptogramin combination, comprising at least one group B component of streptogramins combined with the group A component of general formula (II), in the pure state or in the presence of one or more compatible and pharmaceutically acceptable diluents or adjuvants. These compositions may be used orally or topically. The can contain the combinations according to the invention in the state of a physical mixture of the powders, of a coprecipitate or of a cocrystallizate.

As compositions for oral administration, tablets, hard gelatin capsules, pills, powders, lyophilizates or granules may be used. In these compositions, the active product according to the invention may be mixed with one or more inert diluents or adjuvants such as sucrose, lactose or starch. These compositions can also comprise substances other than diluents, for example a lubricant such as magnesium stearate.

The compositions for topical administration can be, for example, creams, ointments or lotions.

In human or veterinary therapy, the compositions according to the invention are especially useful in the treatment of infections of bacterial origin, in particular severe infections caused by Gram-positive cocci: staphylococcal infections (in particular infections caused by methicillin-resistant staphylococci), streptococcal infections (in particular against penicillin- and macrolide-resistant pneumococci); they are also especially useful in the treatment of infections caused by Haemophilus, *Moraxella catarrhalis, Neisseria gonorrhoeae, Chlamydia trachomatis, Mycoplasma hominis, Mycoplasma pneumoniae* and *Ureaplasma urealyticum*.

The compositions according to the invention may be employed, in particular, in the treatment of upper and lower respiratory infections (for example treatment of pulmonary infections), in the treatment of skin infections, in the long-term treatment of bone or joint infections, in the treatment or prophylaxis of endocarditis in dental and urinary surgery, in the treatment of sexually transmitted diseases and also in the treatment of the opportunistic bacterial and parasitic infections occurring in AIDS and as prophylaxis of the risk of Staphylococcus in immunosuppressed patients.

Generally speaking, the doctor will determine the dosage he considers most suitable in accordance with the age, weight, degree of infection and other factors distinctive to the subject who is to be treated. Generally, the doses are between 0.4 and 3.5 g of active product taken in 2 or 3 doses daily via the oral route for an adult.

The examples which follow, given without implied limitation, illustrate some compositions according to the invention:

Example A

Opaque hard gelatin capsules containing a 250 mg dose of the cocrystallized PIB/PIIB combination are prepared according to the usual techniques.

Example B

Opaque hard gelatin capsules containing a 250 mg dose of the cocrystallized factor S/PIIB combination are prepared according to the usual techniques.

Example C

Tablets containing a 384 mg dose of active product and having the following composition are prepared according to the usual techniques:

| | |
|---|---|
| PIB/PIIB (45%/55%) | 384 mg |
| Hydroxypropylmethylcellulose | 25 mg |
| Magnesium stearate | 35 mg |
| Colloidal silica | 14 mg |
| Starch            qs | 700 mg |

Example D

Tablets containing a 384 mg dose of active product and having the following composition are prepared according to the usual techniques:

| | |
|---|---|
| Factor S/PIIB (45%/55%) | 384 mg |
| Hydroxypropylmethylcellulose | 25 mg |
| Magnesium stearate | 35 mg |
| Colloidal silica | 14 mg |
| Starch            qs | 700 mg |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A method for purifying streptogramins, comprising the step of cocrystallizing at least one streptogramin of the formula (I)

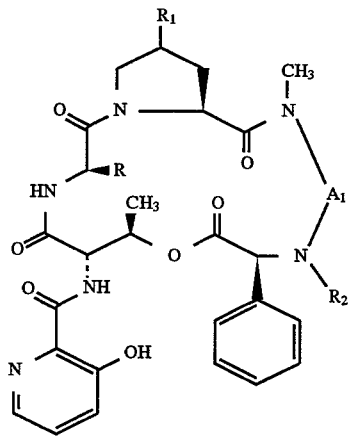
(I)

wherein $A_1$ is a radical of the formula

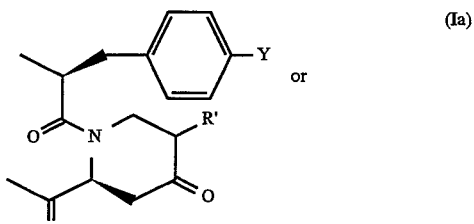
(Ia)
or

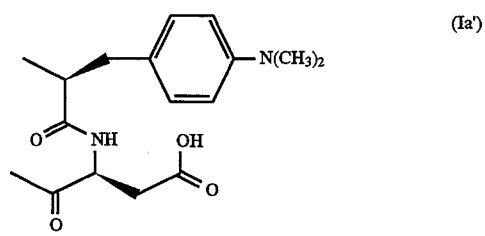
(Ia')

and further wherein R' is a hydrogen atom or a hydroxyl radical and Y is a hydrogen atom, a methylamino radical or a dimethylamino radical, R is an ethyl radical or when R' represents a hydrogen atom, R can also represent a methyl radical, and $R_1$ and $R_2$ each represents a hydrogen atom, or alternatively $A_1$ is a radical of formula:

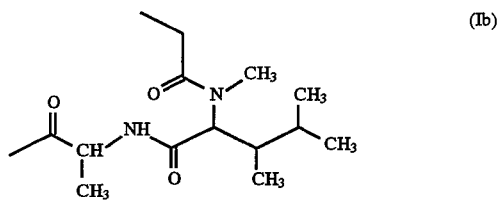
(Ib)

wherein R is an isobutyl radical, and $R_1$ is a hydroxyl radical and $R_2$ is a methyl radical, with at least one streptogramin of the formula (II)

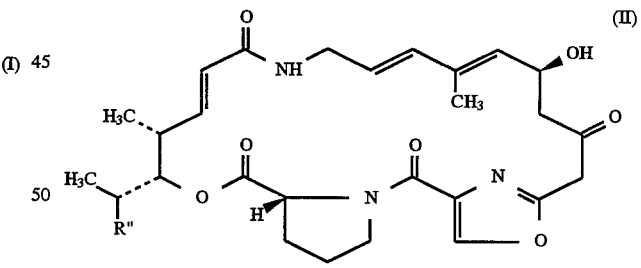
(II)

wherein R" is a hydrogen atom, a methyl radical or an ethyl radical; to form a cocrystallizate of said at least one streptogramin of the formula (II) and said at least one streptogramin of the formula (I).

2. A method for purifying at least one streptogramin of the formula (II)

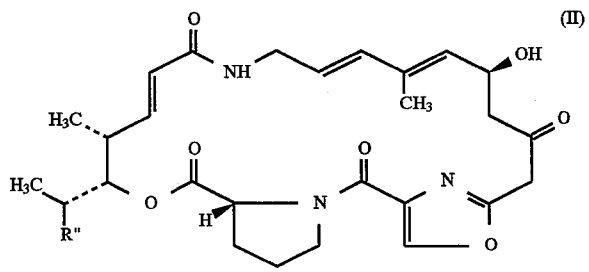

(II)

wherein R" is a hydrogen atom, a methyl radical or an ethyl radical comprising the step of cocrystallizing a crude mixture containing at least one said streptogramin of the formula (II) with at least one streptogramin of the formula (I)

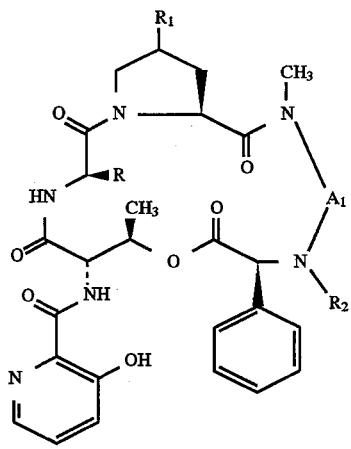

(I)

wherein $A_1$ is a radical of the formula

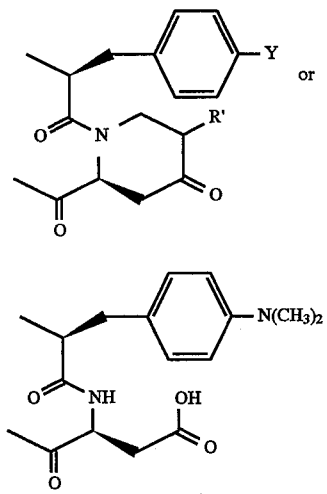

(Ia)

or (Ia')

and further wherein R' is a hydrogen atom or a hydroxyl radical and Y is a hydrogen atom, a methylamino radical or a dimethylamino radical, R is an ethyl radical or when R' represents a hydrogen atom, R can also represent a methyl radical, and $R_1$ and $R_2$ each represents a hydrogen atom, or alternatively $A_1$ is a radical of formula:

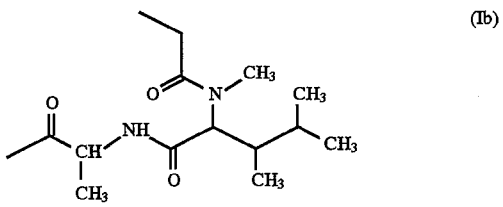

(Ib)

wherein R is an isobutyl radical, and $R_1$ is a hydroxyl radical and $R_2$ is a methyl radical, to form a cocrystallizate of said at least one streptogramin of the formula (II) and said at least one streptogramin of the formula (I).

3. The method of claim 2 further comprising the step of separating said at least one streptogramin of the formula (II) from said cocrystallizate, whereby said at least one streptogramin of the formula (II) is further purified.

4. The method of claim 3, wherein said separating step comprises extracting in an acid medium said at least one streptogramin of the formula (II) from said at least one streptogramin of the formula (I).

5. The method of claim 3, further comprising the steps of converting to powder form said at least one streptogramin of the formula (II) and mixing said powder of said at least one streptogramin of the formula (II) with a second powder of at least one streptogramin of the formula (I), said at least one streptogramin of formula (I) having been purified beforehand, to form a mixture of powders.

6. The method of claim 5 wherein said mixture of powders contains a proportion of 10:90 to 90:10, respectively, by weight of the streptogramin of the formula (II) to the streptogramin of the formula (I).

7. The method of claim 2, further comprising the step of coprecipitating said cocrystallizate with an amount of at least one streptogramin of the formula (I) having been purified beforehand or an amount of at least one streptogramin of the formula (II) having been purified beforehand sufficient to form a coprecipitate.

8. The method of claim 7, wherein said coprecipitate contains a proportion of 10:90 to 90:10, respectively, by weight of the streptogramin of the formula (II) to the stroptogramin of the formula (I), and wherein said weight proportion in said coprecipitate does not contain a molar ratio of the streptogramin of the formula (I) to the streptogramin of the formula (II) on the order of 1:2.

9. The method of claim 8, wherein said weight proportion in said coprecipitate is 20:80 to 80:20.

10. The method of claim 7 wherein the step of coprecipitation occurs from a solution of said at least one streptogramin of the formula (I) and said at least one streptogramin of the formula (II) in methyl isobutyl ketone, acetone, or methylene chloride.

11. A method for purifying at least one streptogramin of the formula (II)

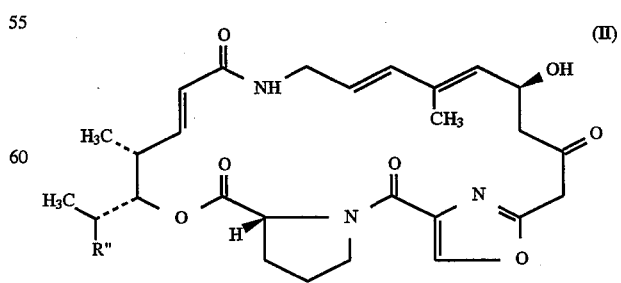

(II)

wherein R" is a hydrogen atom, a methyl radical or an ethyl radical comprising the step of cocrystallizing a mixture containing at least 30% of at least one streptogramin of the formula (II) in a solvent with an amount of at least one streptogramin of the formula (I)

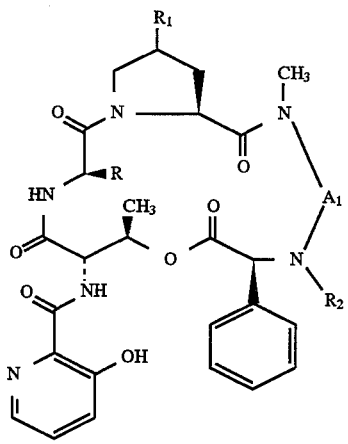
(I)

wherein $A_1$ is a radical of the formula

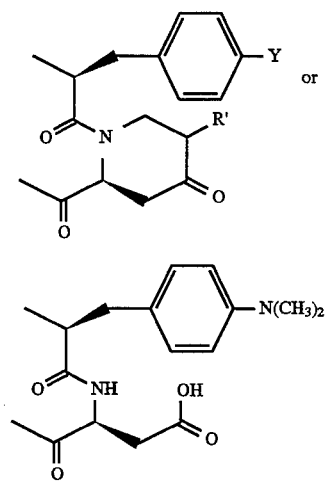
(Ia) or (Ia')

and further wherein R' is a hydrogen atom or a hydroxyl radical and Y is a hydrogen atom, a methylamino radical or a dimethylamino radical, R is an ethyl radical or when R' represents a hydrogen atom, R can also represent a methyl radical, and $R_1$ and $R_2$ each represents a hydrogen atom, or alternatively $A_1$ is a radical of formula:

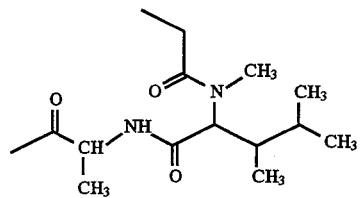
(Ib)

wherein R is an isobutyl radical, and $R_1$ is a hydroxyl radical and $R_2$ is a methyl radical, sufficient to form a cocrystallizate of said at least one streptogramin of the formula (II) and said at least one streptogramin of the formula (I).

12. The method of claim 11 wherein said amount of at least one streptogramin of the formula (I) is also sufficient to maintain, after cocrystallization, the residual concentration of said at least one streptogramin of the formula (I) at a level less than the solubility of said streptogramin compound in said solvent.

13. The method of claim 11 wherein said solvent is an organic solvent, said solvent being a ketone, an ester, a chlorinated organic solvent, or a nitrile.

14. The method of claim 13, wherein said organic solvent is a ketone, said ketone being acetone, methyl ethyl ketone, or methyl isobutyl ketone.

15. The method of claim 13, wherein said organic solvent is a chlorinated organic solvent, said chlorinated organic solvent being methylene chloride, chloroform, or 1,2-dichloroethane.

16. The method of claim 13, wherein said organic solvent is acetonitrile.

17. The method of claim 11, comprising the further steps of:

dissolving the cocrystallizate in an organic solvent, extracting with an acidic medium, and recovering said at least one purified streptogramin of the formula (II) by precipitation from the organic phase.

18. The method of claim 17 wherein said organic solvent is methyl isobutyl ketone or dichloroethane.

19. The method of claim 17 wherein said acid medium is sulphuric acid or hydrochloric acid.

20. The method of claim 17 wherein said recovery by precipitation is effected by treating said organic phase with a solvent.

21. The method of claim 20, wherein said solvent used to treat said organic phase is hexane.

22. The method of claim 11, wherein said at least one streptogramin of the formula (I) is pristinamycin IA, IB, IC, ID, virginiamycin $S_1$ or virginiamycin $S_4$.

23. The method of claim 22, wherein said at least one streptogramin of the formula (II) is pristinamycin IIB.

24. The method of claim 23, wherein said at least one streptogramin of the formula (I) is pristinamycin IB.

* * * * *